(12) United States Patent
Parker

(10) Patent No.: US 6,755,198 B2
(45) Date of Patent: Jun. 29, 2004

(54) DIAPERING RESTRAINT SYSTEM

(76) Inventor: Shannon Cox Parker, 1142 Indian Autumn Trace, Houston, TX (US) 77062

( * ) Notice: Subject to any disclaimer, the term of this patent is extended or adjusted under 35 U.S.C. 154(b) by 0 days.

(21) Appl. No.: 10/284,785

(22) Filed: Oct. 31, 2002

(65) Prior Publication Data

US 2004/0084052 A1 May 6, 2004

(51) Int. Cl.[7] ................................................. A61F 5/37
(52) U.S. Cl. ...................................... 128/870; 128/876
(58) Field of Search ................................ 128/845, 846, 128/869, 873–876

(56) References Cited

U.S. PATENT DOCUMENTS

| 2,102,281 A | 12/1937 | Pringle | 128/875 |
|---|---|---|---|
| 2,547,466 A | 4/1951 | Hoder | 128/872 |
| 2,758,595 A | 8/1956 | Lovett | 5/655 |
| 2,846,700 A | 8/1958 | De Puy | 5/424 |
| 3,779,540 A | 12/1973 | Boudreau | 5/655 |
| 4,205,669 A | 6/1980 | Hamann | 5/603 |
| 4,712,258 A | 12/1987 | Eves | 5/424 |
| D393,561 S | 4/1998 | Hayes | D6/596 |
| 5,799,654 A | 9/1998 | Kassan | 128/869 |
| 6,009,874 A | 1/2000 | Sartin | 128/869 |

*Primary Examiner*—Michael A. Brown

(57) ABSTRACT

A system for restraining the upper torso of a child or infant for diapering activities. The system provides a stable base (10) onto which the child is laid, and provides restraining straps (16) which are attached to the base (10) and arranged over the chest of the child in a crisscrossing manner. The child is prevented from rolling, sitting and sliding by the combined action of the restraining straps (16) and the stable base (10). The system effectively controls movement of the child's upper torso and maintains the child in a proper diapering position.

6 Claims, 4 Drawing Sheets

DIAPERING RESTRAINT SYSTEM

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

1. Field of Invention

This invention relates to child restraint systems, specifically to such restraint systems which are used for diapering activities.

BACKGROUND

2. Description of Prior Art

Many a care-giver has struggled to maintain a writhing infant in a suitable position for a diaper change. As babies learn to move about, they are less inclined to remain still when placed upon their backs. Commonly during a diapering activity, a growing infant will roll over, sit up, or push himself in a head-wise direction by planting his heels and thrusting his legs. In addition to causing considerable inconvenience to the care-giver, such movements create significant hazards. Sadly, many infants have suffered serious injuries after falling from elevated changing surfaces.

The patent record reveals a long history of inventions which have aimed to address these issues of safety and convenience. Many early designs including Pringle U.S. Pat. No. 2,102,281, Hoder U.S. Pat. No. 2,547,466, and Lovett U.S. Pat. No. 2,758,595 employ upper-torso restraint systems. Each of these devices requires that several components be interlocked to create a secure restraint. Such operations are particularly difficult for care-givers to perform when a child is writhing vigorously. As a result, any convenience such devices might offer through restraint of the child is likely negated by the inconveniences encountered while interlocking the components.

A trend towards less complexity is demonstrated in De Puy U.S. Pat. No. 2,846,700, Boudreau U.S. Pat. No. 3,779,540, and Eves U.S. Pat. No. 4,712,258; each of which utilizes a single cross-torso strap restraint. A basic version of the cross-torso strap restraint is in wide use today. Despite its popularity, this system does not provide adequate restraint for an active infant. It fails to prevent the child from rolling onto his belly, from sitting upright if the strap is located at or below his navel, or from thrusting himself in a head-wise direction. Though widely available and relatively simple by design, the cross-torso strap restraint has not adequately addressed the needs of care-givers as revealed by the continuing patent record.

Several later 20th century patents such as Hamann U.S. Pat. No. 4,205,669 and Kassan U.S. Pat. No. 5,799,654 call for larger-scale structures and mechanisms. The Hamann invention utilizes a separation panel designed to be placed across the child's torso in order to keep the child's arms separated from his lower half. Additionally, it includes ankle straps to separate the child's feet and fasten them to the changing surface. Such a design limits the care-giver's ability to raise the child's lower half from the changing surface in order to clean the child's bottom. The Kassan invention utilizes a multi-part stirrup device to maintain control over the elevation and separation of the child's ankles. Such a system requires first, that each ankle be captured in the stirrups, and second, that someone or some additional structure provides lifting support for the stirrup device so that the diapering activity can be performed below it. The child can still twist her body, thrust her legs and generally move in an unsuitable way while this device is employed. Both the Hamann and the Kassan inventions are too costly for the average consumer because of the complexity of their designs. Furthermore, the Kassan design is somewhat imposing and may be threatening to a young child.

Recently, an interest in the upper-torso restraint concept has returned as revealed by Hayes U.S. Pat. No. Des. 393561 and Sartin U.S. Pat. No. 6,009,874. The Hayes design utilizes two strap restraints which pin the child's shoulders down to the changing surface at points above each shoulder and below each armpit. Such restraints against the sensitive area beneath the arms may cause discomfort and aggravation, making the diapering process taxing for both child and care-giver.

The Sartin system employs a base structure upon which a child is laid and a tank-top shaped chest cover which is attached to the base structure at each shoulder and at each lateral side such that the child is sandwiched between the chest cover and the base structure. This four point attachment scheme may be too tedious for some caregivers who will decide not to bother with the four separate attachments after a few usages. Furthermore, repeated removal and reattachment of the detachable chest cover from the base structure increases the likelihood that the chest cover will be lost or misplaced away from the changing area. A hazardous situation could arise if a care-giver leaves a child unattended on an elevated changing surface to retrieve a misplaced chest cover.

As described in this section, each of these diaper-changing restraint systems suffers from one or more of the following disadvantages:

a) The design requires too many operational steps thereby negating any added convenience.

b) The design does not provide adequate restraint features, allowing movements such as rolling, sliding or sitting upright. Such movements are inconveniences for the care-giver, and, more critically, safety hazards for the child.

c) The design is too complex to manufacture at a cost that is reasonable for the consumer.

d) The design is imposing and may frighten the child.

e) The design is uncomfortable for the child.

f) The device has separable components which can be lost or misplaced after usage.

Objects and Advantages

Accordingly, several objects and advantages of the present invention are:

a) to provide improved convenience with a simple system requiring few operational steps;

b) to provide improved child safety during the diapering activity with adequate restraint features that resist movements such as rolling, sliding and sitting upright;

c) to provide an affordable diapering restraint system by limiting the part count and minimizing the design complexity;

d) to provide a diapering restraint system within which a child can feel unthreatened;

e) to provide a comfortable diapering restraint system that gently maintains the child in a proper diapering position;

f) to provide a fully connected diapering restraint system that maintains all components with the device at all times.

Further objects and advantages of the present invention are to provide a system that can be tailored to rest permanently upon a dresser or table top, or to fold neatly into the child's travel bag.

SUMMARY

In accordance with the present invention a diapering restraint system comprises a stable base upon which a child can be laid, and a plurality of restraining straps which are attached to the base and arranged such that they can be secured across the upper-torso of the child in a crisscrossing manner.

DRAWINGS

Drawing Figures

Figure 1:
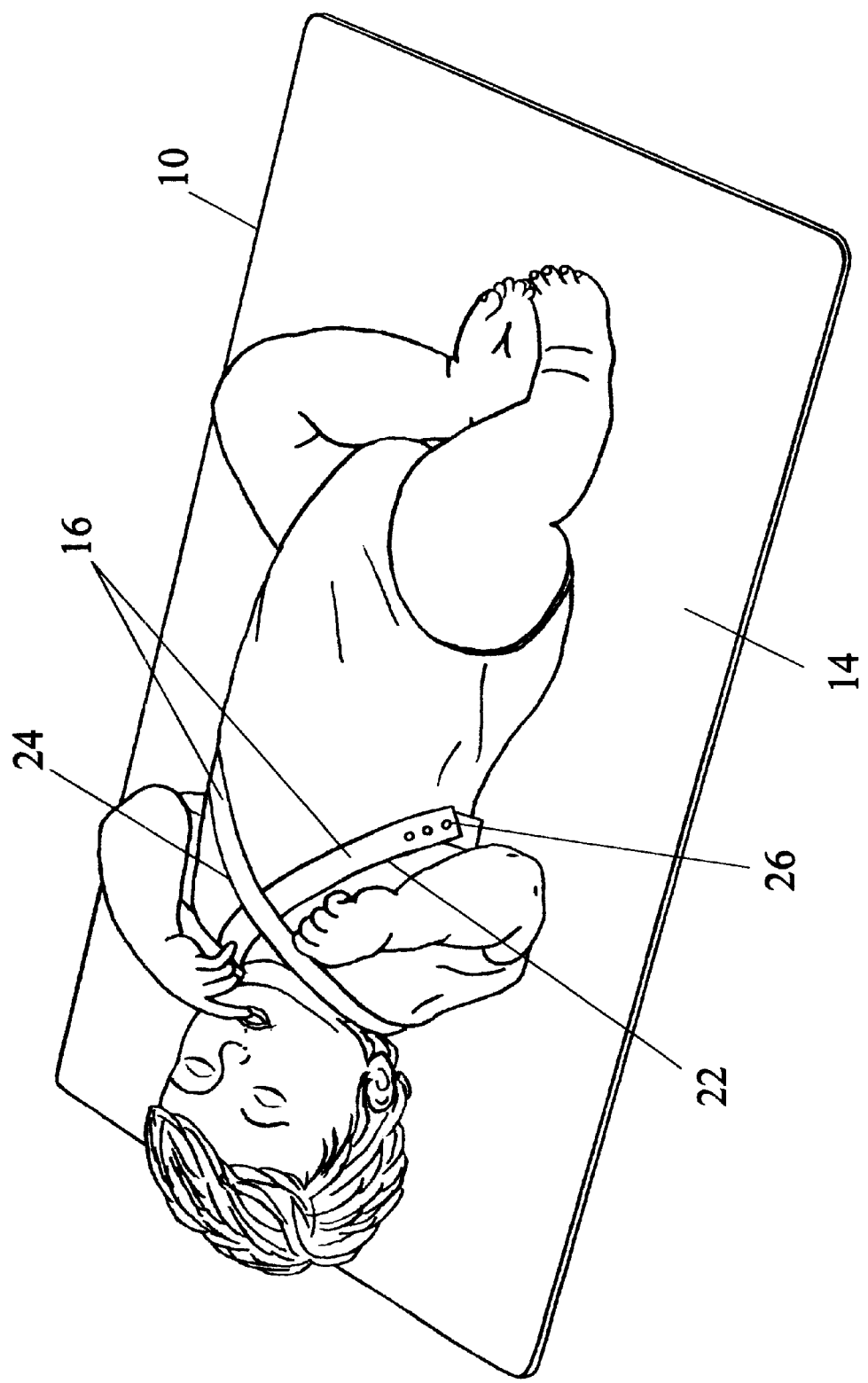
FIG. 1 is a perspective view of the present invention according to the preferred embodiment. The invention is shown in use with the straps secured to restrain a child upon the base.

REFERENCE NUMERALS IN DRAWINGS 10 base
12 stabilizing structure
14 top surface
16 restraining straps
18 cushioning material
20 base casing
22 first crossing strap
22A shoulder extension (first crossing strap)
22B torso extension (first crossing strap)
24 second crossing strap
24A shoulder extension (second crossing strap)
24B torso extension (second crossing strap)
26 fastening means
28 connection means
30 adjustment means
32 cushioned pad
34 cushioned pad casting
36 through-openings
38 strap attachment locations

DETAILED DESCRIPTION

Figure 2:
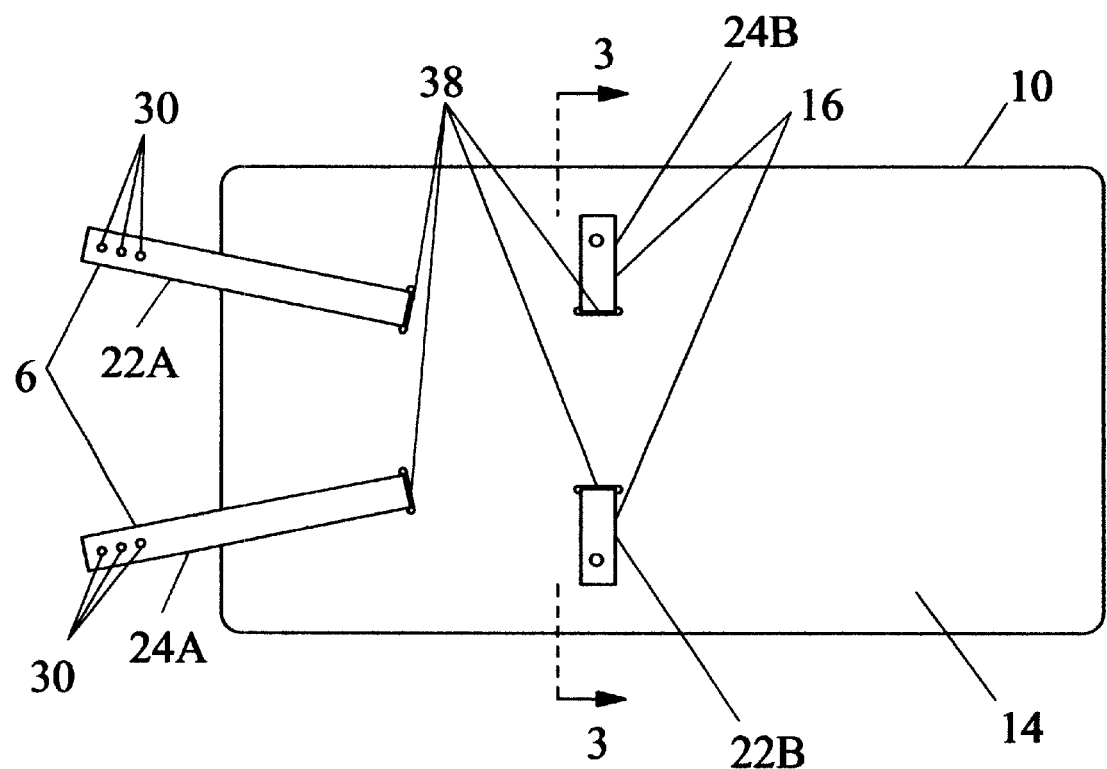
FIG. 2 is a plan view of the preferred embodiment.
Figure 3:
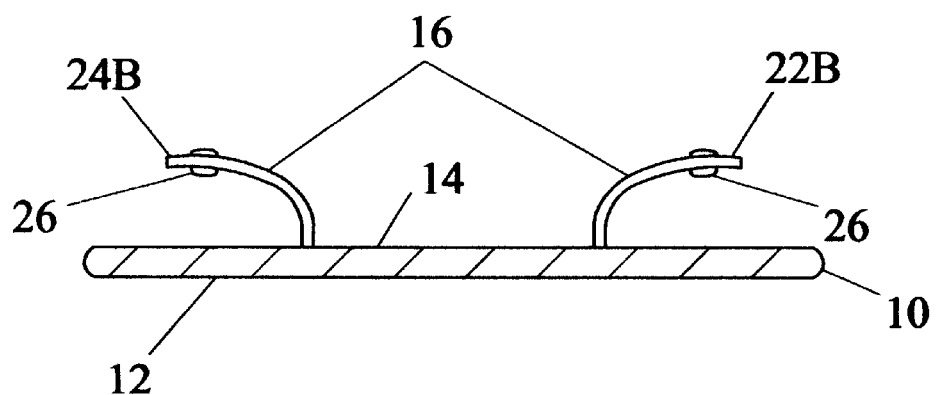
FIG. 3 is a cross-sectional view taken on line 3—3 in FIG. 2.

FIGS. 1 through 3—Preferred Embodiment

A preferred embodiment of the present invention is illustrated in FIGS. 1 through 3. The form of the device comprises a stable base 10 with a top surface 14 upon which a child can be laid, and restraining straps 16 that are attached to the base 10 to secure the child in a proper diapering position as demonstrated in FIG. 1. The base 10 is generally rectangular in shape and sized to fit upon diaper changing tables and dressers. However, the device may be scaled larger or smaller as needed for specific usages. In the preferred embodiment, the base 10 solely comprises a stabilizing structure 12 which is labeled in FIG. 3. The stabilizing structure 12 is sized to resist the overturning forces which can be produced by a child moving vigorously upon the base 10 when secured by the restraining straps 16. The stabilizing structure 12 may be constructed of any material providing substantial rigidity for the application. Such materials include wood products, plastics, and metals. The thickness of the stabilizing structure 12 is dependent upon the strength characteristics of the material from which it is made. The present invention may further utilize the working surface of a changing table or dresser for the stabilizing feature of the base 10. Alternatively, the stabilizing structure 12 can derive its stability and rigidity from a framework construction rather than from a structural member of uniform cross-section. Another suitable alternative for the stabilizing structure 12 is a molded plastic form with a top surface 12 that is contoured to receive the child's body.

Attached to the base 10 are restraining straps 16 generally having a wide flat cross section and an elongated length. The restraining straps 16, including a first crossing strap 22 and a second crossing strap 24 shown in FIG. 1, are sized and arranged to be secured across the chest of the child in a crisscrossing manner. The first crossing strap 22 is attached to the base 10 at the child's left shoulder and at the right side of the child's torso. The second crossing strap 24 is attached to the base 10 at the child's right shoulder and at the left side of the child's torso. In the preferred embodiment, the straps 22 and 24 are constructed of a flexible webbing material. Alternatively, the straps can be constructed from fabric or any suitably flexible and durable material that is safe for use with young children.

The restraining straps 16 are attached to the base 10 at the strap attachment locations 38 which are labeled in FIG. 2. The attachments can be constructed as permanent or releasable attachments. Permanent attachments may be formed with tacks, rivets or adhesives while releasable attachments may include snaps, buckles, or touch-close materials. Either manner of attachment must allow for an effective transfer of force between the restraining straps 16 and the base 10. A simplified attachment scheme is represented in FIG. 3.

In the preferred embodiment, both the first crossing strap 22 and the second crossing strap 24 are comprised of two strap segments which are connected with a releasable fastening means 26. These strap segments are illustrated in FIG. 2, including shoulder extensions 22A and 24A, and torso extensions 22B and 24B. The fastening means 26, labeled in FIGS. 1 and 3, is shown as provided by snap fasteners. However, other releasable fasteners may be used such as buckles, buttons and touch-close materials. As an alternative design, both the first crossing strap 22 and the second crossing strap 24 can be constructed as un-segmented elements (not pictured). With this alternative, the releasable fastening means 26 should be provided for each crossing strap at one or both of its strap attachment locations 38.

An adjustment means 30 may be provided with the restraining straps 16 to allow the strap lengths to be customized to fit securely across children of various sizes. The adjustment means 30, labeled in FIG. 2, is provided by a series of snap fasteners, where shoulder extensions 22A and 24A each include several female snap fastener halves, and where torso extensions 22B and 24B each include a single male snap fastener half. This arrangement of male and female halves can be swapped or rearranged without compromising function. Alternatively, the adjustment means 30 may be provided in other ways as with slide-locking buckles, with large contact areas of touch-close materials, and with the use of elastic material in the construction of the straps to allow the straps to stretch to a range of lengths.

Operation—FIGS. 1–3

The manner for using the diapering restraint system of FIGS. 1 through 3 is straightforward. The device according to the preferred embodiment must first be rested upon a substantially rigid and horizontal surface such as a table top or a floor. The next step is to position the child upon the device such that the child's shoulders and the sides of the child's torso are in line with the strap attachment locations 38. After the child is positioned, the restraining straps 16 are arranged and secured across the child's upper body in a crisscrossing manner. Specifically, the first crossing strap 22 is secured by fastening the shoulder extension 22A to the torso extension 22B. In this embodiment, the first crossing strap is adjusted for fit and fastened in one procedure using snap fasteners. As mentioned previously, the adjustment means 30 can be provided in other ways as with slide-locking buckles, touch-close fasteners or elastic. Where other adjustment means 30 are provided, the first crossing strap 22 may be adjusted for proper fit in a separate step. Next, the second crossing strap 24 is secured in the same manner as the first crossing strap 22. Namely, the shoulder extension 24A is fastened to the torso extension 24B, and the strap is adjusted for fit as needed with the adjustment means 30. Once the restraining straps 16 are secured and adjusted, the child is properly restrained within the device and the diapering activity can be performed. It should be noted that the order by which the restraining straps are secured is arbitrary and has been specified in this text for illustrative purposes only.

To remove the child from the device, the restraining straps 16 must be unfastened so that the child is no longer restrained and thus can be removed.

FIGS. 4 through 8—Additional Embodiments

Figure 4:
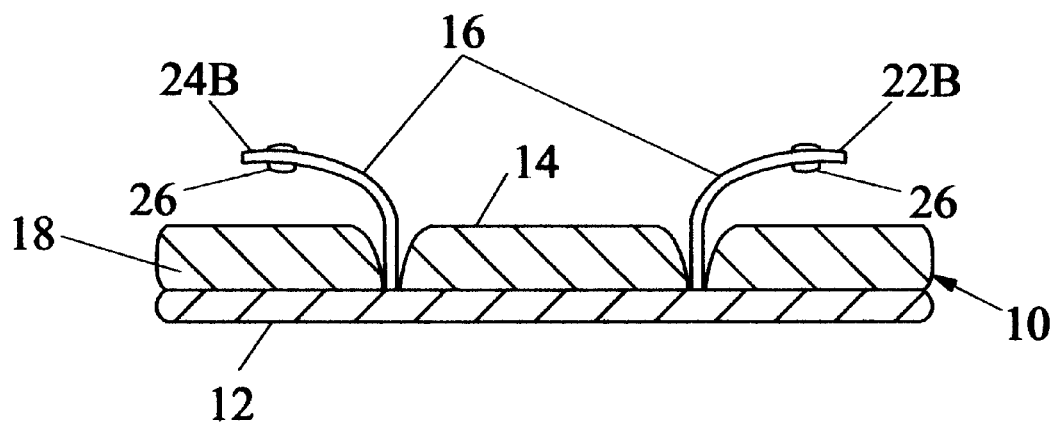
FIGS. 4 through 6 are cross sectional views similar to FIG. 4 but showing variants of the device shown in FIG. 4.

The form of the device shown in FIG. 4 is very similar to the form depicted in FIGS. 1 through 3 except that the base 10 includes a layer of cushioning material 18. This layer of cushioning material 18 is located above the stabilizing structure 12 and extends the full length of the device to provide added comfort for the child that is laid upon it. The cushioning material 18 is preferably foam of the type commonly used in mattress and upholstery padding. Other cushioning materials which may be suitable for the application include fills such as those used in pillows and stuffed toys. In the form of the device shown in FIG. 4, the top surface 14 may be provided by a cleanable, flexible and waterproof material to offer a suitable work surface for diaper changing activities. Vinyl fabrics are quite suitable for top surface 14.

Figure 5:
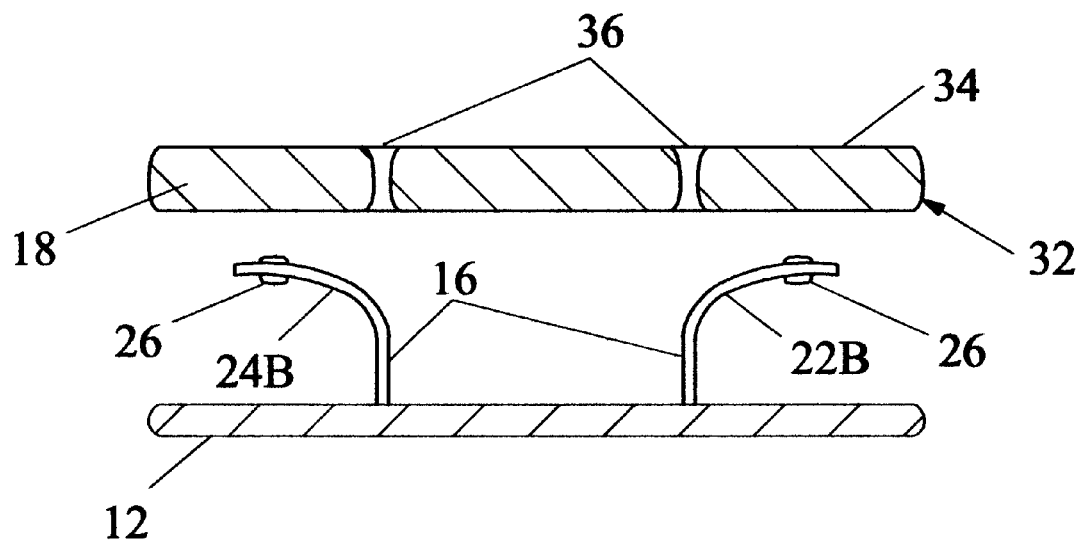

The cushioning feature of the device in FIG. 5 is provided by a cushioned pad 32 that is separable from the rest of the device. Similarly to the form of the device in FIG. 4, the cushioned pad 32 includes a layer of cushioning material 18. The cushioning material 18 is surrounded by a cushioned pad casing 34 that is constructed preferably from a flexible, cleanable and waterproof material like vinyl. The cushioned pad 32 has through-openings 36 through which the restraining straps 16 can be passed. FIG. 5 illustrates the through-openings 36 that are aligned with torso extensions 22B and 24B.

Figure 6:
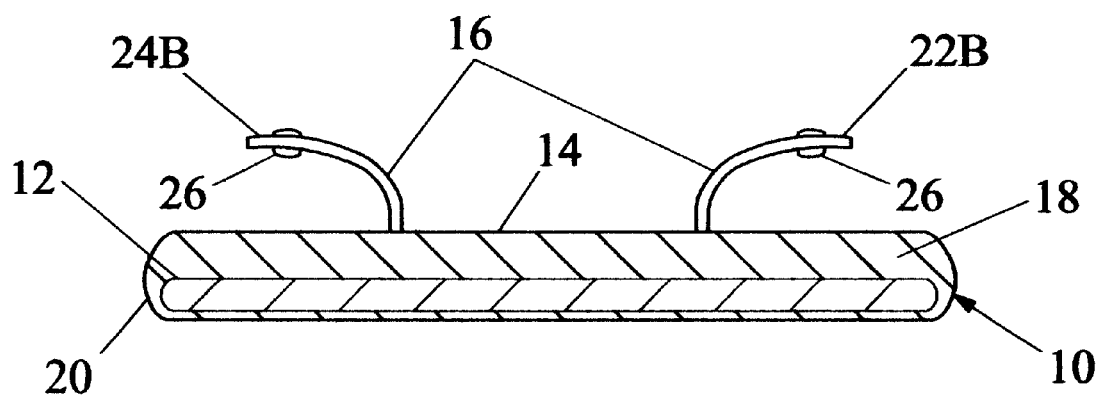

An alternative arrangement of the cushioning feature and the base 10 is illustrated in FIG. 6. This form of this device is similar to that of FIG. 4 except that the base 10 includes a base casing 20 which envelopes both the cushioning material 18 and the stabilizing structure 12. Furthermore, the restraining straps 16 are attached to the top surface 14 of the base 10 which is formed by the base casing 20. The attachment of the restraining straps 16 to the base casing 20 may be fashioned in any number of ways, including stitching, gluing, and fusing. Any such attachment must be strong enough to transfer forces from the restraining straps 16 into the base casing 20 without failure of the attachment. Similarly, the base casing 20 must be constructed of a material of substantial durability to withstand these forces and to transfer them to the stabilizing structure 12. Additionally, this material for the base casing 20 should be cleanable, flexible and waterproof.

Figure 7:
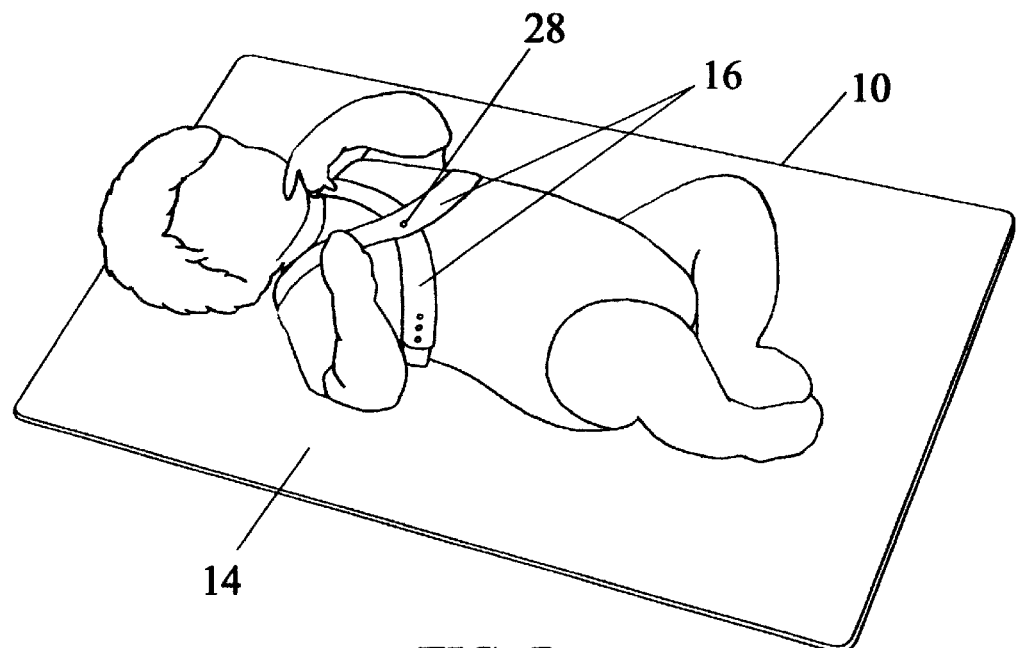
FIG. 7 is a perspective view of an alternate embodiment in use. The device is shown having curved straps and a central connection at the midline of the child's chest.
Figure 8:
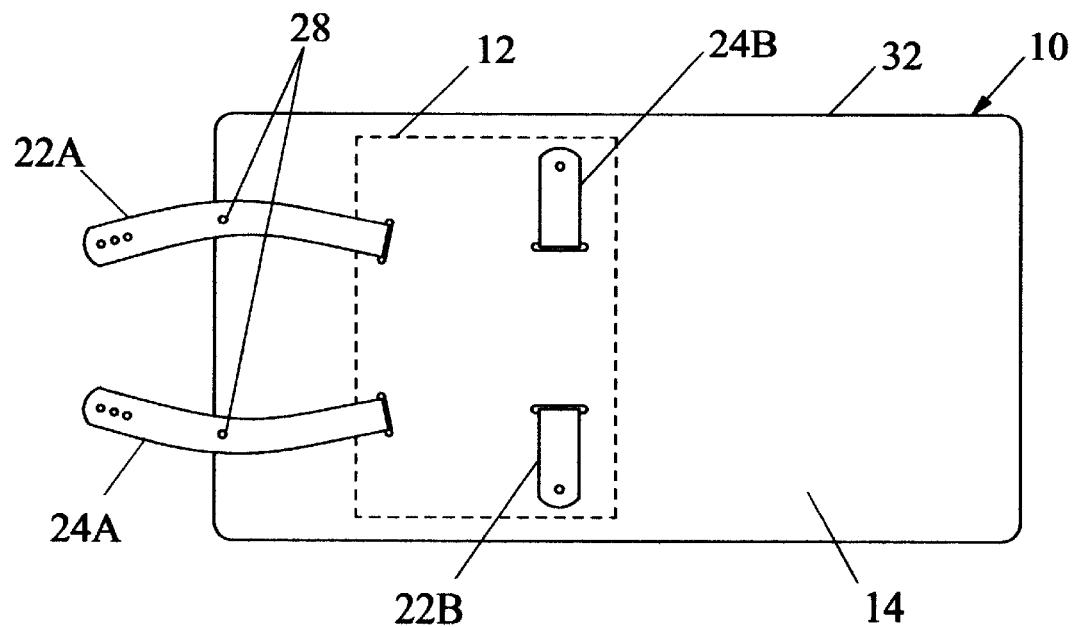
FIG. 8 is a plan view of the device shown in FIG. 7.

The form of the device shown in FIGS. 7 and 8 is very similar to that of the other figures, particularly FIGS. 1 and 2. However, the device of FIGS. 7 and 8 includes a connection means 28 to releasably connect the restraining straps 16 together at the location where the straps cross each other. This connection means 28 improves the restraining ability of the device by further limiting the range of movement of the child's upper body. With the connection means 28 employed, the restraining straps 16 are held in a fixed position relative to each other and do not slide back and forth as the child attempts to roll from side to side. A snap fastener is shown in FIG. 7 for the connection means 28 but other suitable connectors like buttons, buckles and touch-close materials could be used instead.

In addition, the device of FIGS. 7 and 8 is illustrated with an alternative design shape for the restraining straps 16. These straps are shown constructed from a fabric material and shaped to conform to a child's body. The plan view of FIG. 8 shows the conforming shape of the restraining straps 16 by the curved forms of shoulder extensions 22A and 24A.

Moreover, in the form of the device illustrated in FIG. 8, the stabilizing structure 12 is represented by dashed lines forming the shape of a rectangle. In this view, a cushion pad 32 comprises the larger rectangular element of the device while the stabilizing structure 12 comprises the smaller rectangular element below the cushioned pad 32. This stabilizing structure 12 need not be sized the full length and the full width of the device, but must be sized large enough to provide adequate stabilization to the system to thwart the overturning forces produced by the child. A minimally-sized stabilizing structure 12 may provide several advantages over a larger element including reduced weight, reduced material costs, and easier transportability. With this design, the flexible materials including the cushioned pad 32 and the restraining straps 16 can be collapsed and folded around the stabilizing structure 12 to create a diapering restraint system that packs well into a travel bag.

It should be understood that the features highlighted in FIGS. 7 and 8, namely the connection means 28, the alternative design shape of the restraining straps 16, and the stabilizing structure 12 of reduced size, may be combined with any other variation of the present invention.

Operation of the Additional Embodiments

The manners for using the variations of the device illustrated in FIGS. 4 through 6 are identical to the manner for using the device according to the preferred embodiment. However, operation of the device of FIGS. 7 and 8 is similar to that according to the preferred embodiment but includes an additional step to connect the restraining straps 16 together by the connection means 28 at the location where the straps cross. This step to connect the restraining straps 16 together can be performed after the child is properly positioned upon the device.

Conclusion, Ramifications, and Scope

Accordingly, the reader will see that the diapering restraint system of this invention presents a number of advantages over the heretofore known restraint systems, in that:

a) the combined action of the crisscrossing straps and the stabilizing structure acts to maintain a child in a proper diapering position by thwarting the child's attempts to roll, sit, and slide, thereby improving child safety and caregiver convenience during the diapering activity;

b) the simple design with common material selection makes the system economical to manufacture;

c) the straightforward design renders the system easy to operate;

d) the features of the design are unthreatening;

e) the arrangement of the straps creates a comfortable restraint for the child;

f) the components of the system remain connected together during and between usages thereby providing that no part should be misplaced or lost.

The description presented above is provided to illustrate some of the presently preferred embodiments of this invention and should not be construed as limiting the scope or spirit of the invention. It is appreciated that the invention is susceptible to modification and variation without departing from the scope of the appended claims.

I claim:

1. A diapering restraint system to restrain a child for diapering activities comprising a stable base having both a top surface upon which the child is laid and a stiff stabilizing structure for providing rigidity; the restraint system further including a first crossing strap and a second crossing strap, each crossing strap attached at both ends to said stable base to cooperate with said stiff stabilizing structure, wherein one end of said first crossing strap is attached to the base at the child's left shoulder and the other end is attached to the base at the child's right torso, and wherein one end of said second crossing strap is attached to the base at the child's right shoulder and the other end is attached to the base at the child's left torso, each crossing strap being comprised of a shoulder strap segment and a torso strap segment connected together by releasable fastening means enabling the two strap segments to behave as a continuous strap length, whereby said shoulder strap segment and said torso strap segment of each crossing strap may be fastened together above the upper body of the child in a crisscrossing arrangement thereby restraining the child upon said stable base by the combined action of the two crossing straps and the stabilizing structure.

2. The diapering restraint system of claim 1 wherein both said first crossing strap and said second crossing strap include a releasable connection means at the location where the two crossing straps cross each other when secured over a child, said releasable connection means allowing the crossing straps to be releasably connected together, thereby preventing said first crossing strap and said second crossing strap from slipping relative to each other.

3. The diapering restraint system of claim 1 wherein said stable base further comprises a layer of cushioning material.

4. The diapering restraint system of claim 1 further including a fitted casing adapted to envelope said stable base, wherein said first crossing strap and said second crossing strap are attached to said fitted casing, whereby the two crossing straps cooperate indirectly with said stiff stabilizing structure of said stable base through the casing to provide a combined action to restrain a child.

5. The diapering restraint system of claim 1 wherein said first crossing strap and said second crossing strap are constructed from a flexible material and are shaped to conform to the upper body of a child.

6. The diapering restraint system of claim 1 wherein both said first crossing strap and said second crossing strap include an adjustment means allowing the strap lengths to be adjusted to fit securely across children of various sizes.

* * * * *